United States Patent [19]

Millar

[11] 4,175,566

[45] Nov. 27, 1979

[54] CATHETER FLUID-VELOCITY FLOW PROBE

[75] Inventor: Huntly D. Millar, Houston, Tex.

[73] Assignee: Millar Instruments, Inc., Houston, Tex.

[21] Appl. No.: 679,066

[22] Filed: Apr. 21, 1976

Related U.S. Application Data

[63] Continuation-in-part of Ser. No. 602,655, Aug. 7, 1975, abandoned.

[51] Int. Cl.² .............................................. A61B 5/02
[52] U.S. Cl. ................................ 128/692; 73/194 EM
[58] Field of Search ..................... 128/2.05 F, 2.05 R; 73/194 EM

[56] References Cited

U.S. PATENT DOCUMENTS

| 3,309,924 | 3/1967 | Kolin et al. | 73/194 EM |
| 3,516,399 | 6/1970 | Barefoot | 128/2.05 F |
| 3,696,674 | 10/1972 | Spencer | 128/2.05 F X |
| 3,734,083 | 5/1973 | Kolin | 128/2.05 F |
| 3,805,768 | 4/1974 | Barefoot et al. | 128/2.05 F |
| 3,815,582 | 6/1974 | Schuette | 128/2.05 F |
| 3,945,250 | 3/1976 | Elazar et al. | 73/194 EM |

FOREIGN PATENT DOCUMENTS 477719  8/1977  U.S.S.R. ............................... 128/2.05 F

Primary Examiner—Kyle L. Howell
Attorney, Agent, or Firm—Arnold, White & Durkee

[57] ABSTRACT

A catheter fluid-velocity flow probe is disclosed which has greater sensitivity and which dissipates less heat during operation than flow probes heretofore constructed. These significant results are achieved by providing two electromagnets in the probe to generate two separate magnetic fields. Each electrode is positioned between the poles of an electromagnet in the region of highest magnetic flux density of each electromagnet. The electromagnets are reduced in size, and a tubing may be inserted in the central portion of the probe during construction. This tubing permits the attachment of additional measuring devices to the distal end of the probe to permit multiple measurements in a fluid to be made simultaneously.

32 Claims, 26 Drawing Figures

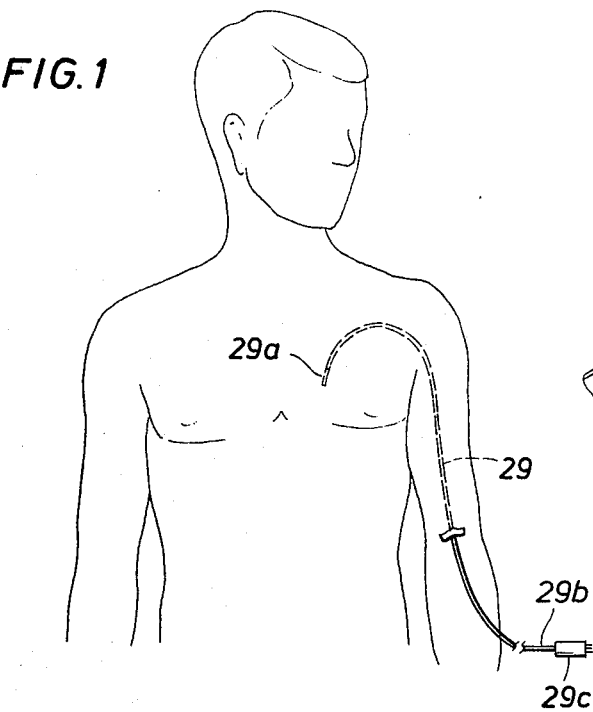
FIG. 1
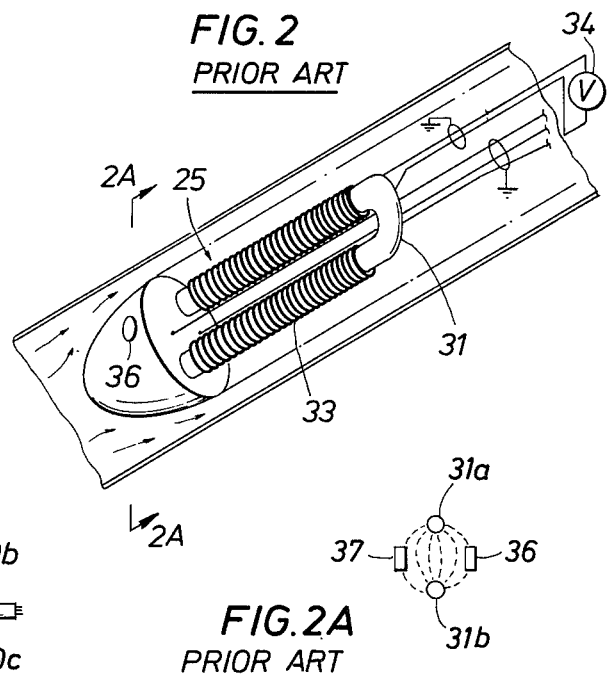
FIG. 2 PRIOR ART
FIG. 2A PRIOR ART
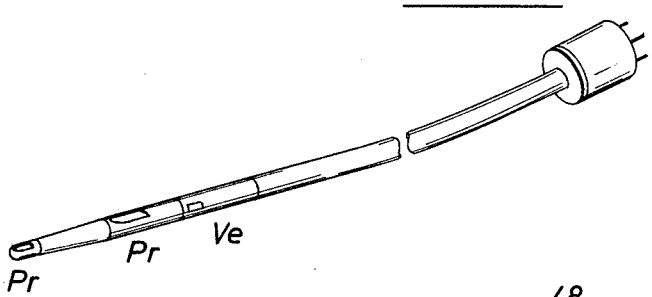
FIG. 3
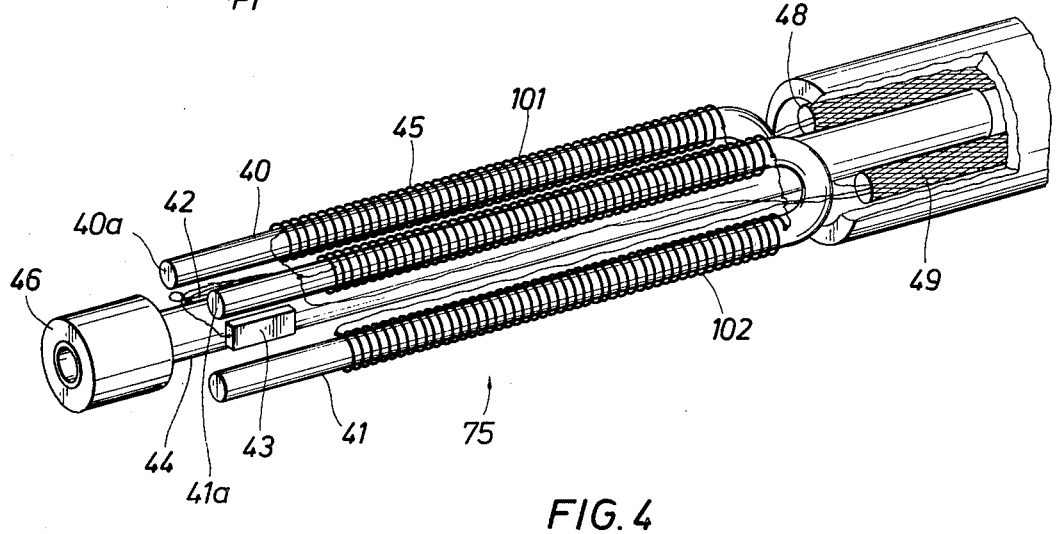
FIG. 4

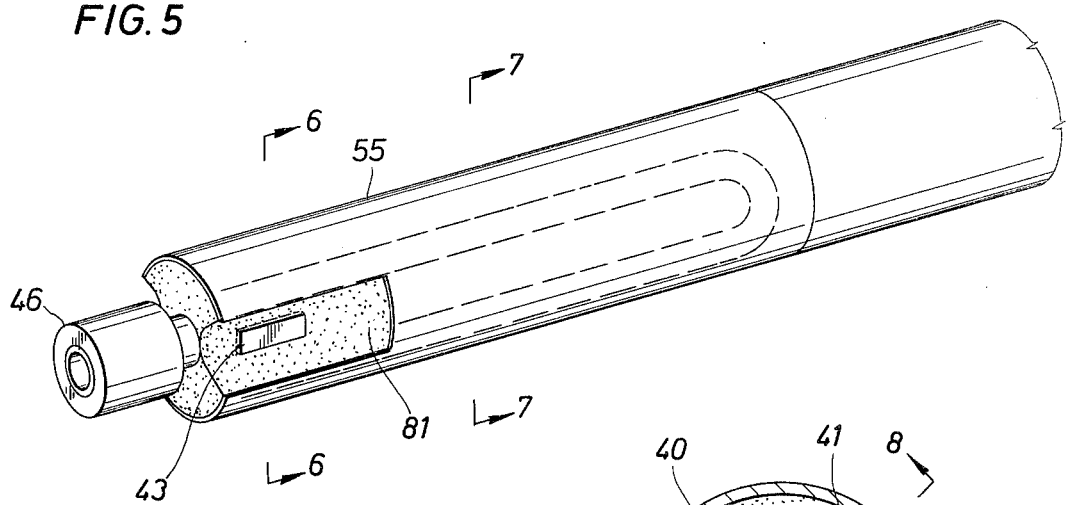
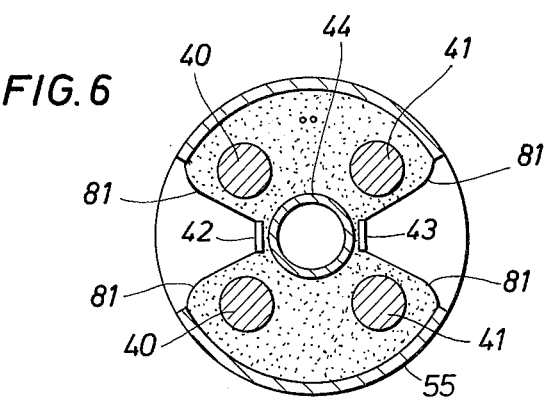
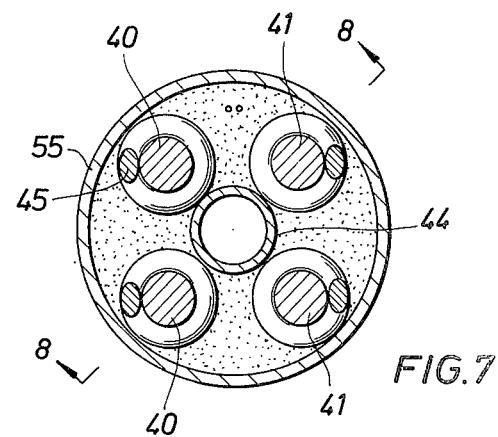
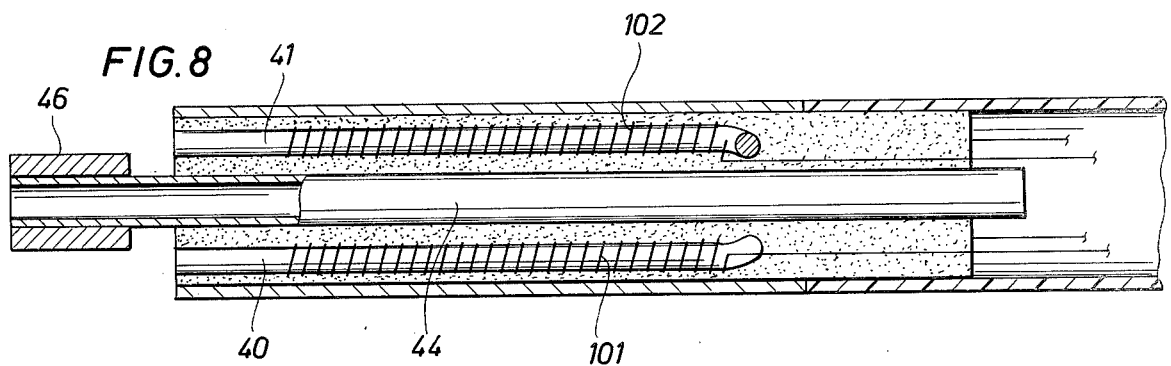
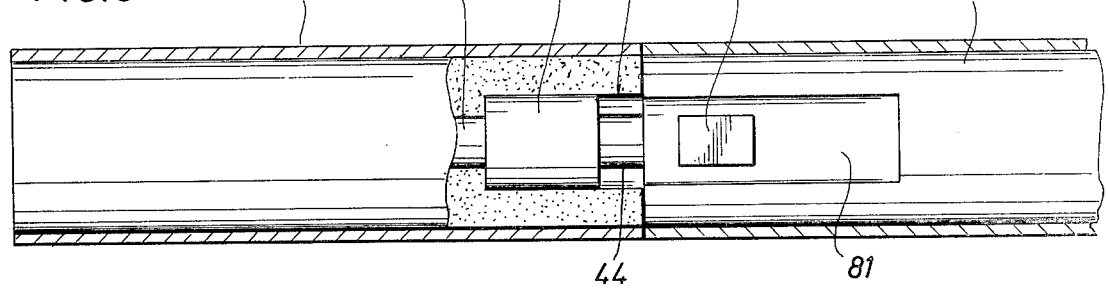

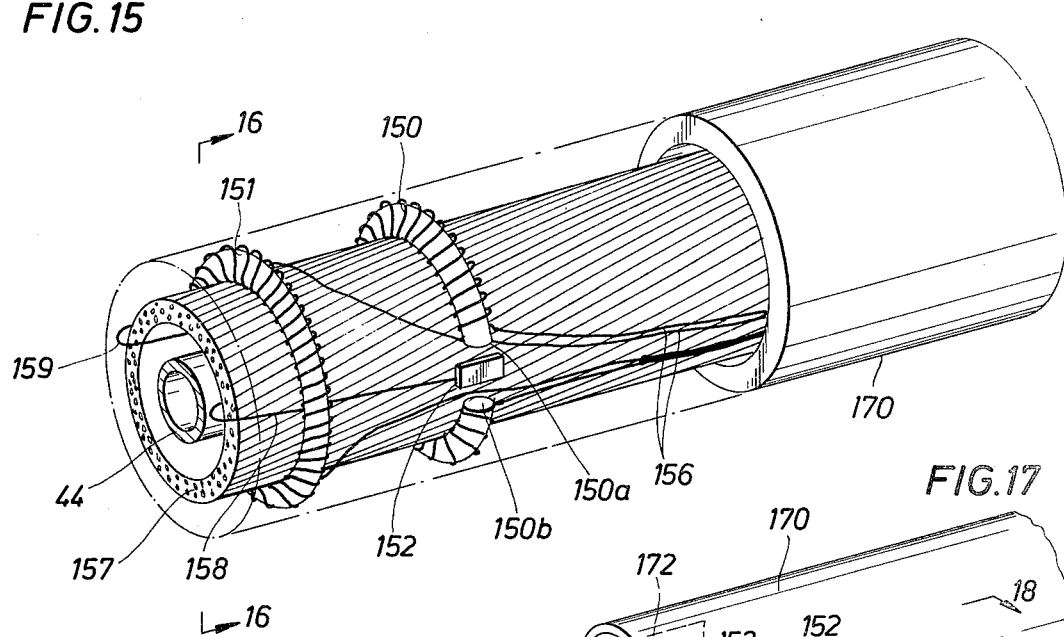
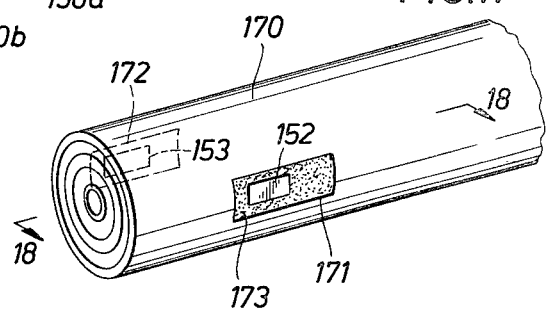
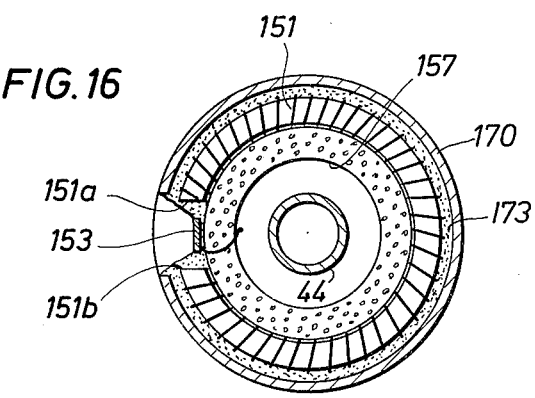
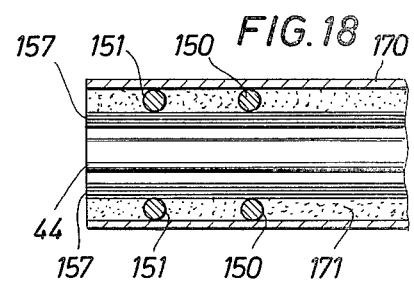
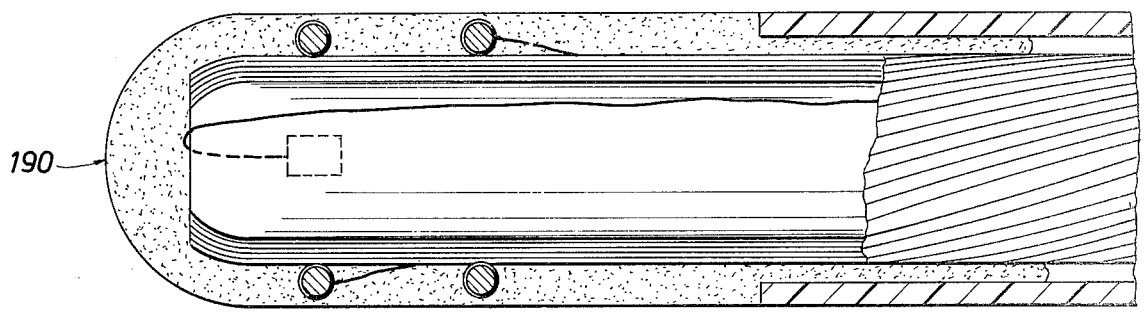

CATHETER FLUID-VELOCITY FLOW PROBE

CROSS REFERENCE TO RELATED APPLICATIONS

This application is a continuation-in-part of application Ser. No. 602,655, filed Aug. 7, 1975 now abandoned.

BACKGROUND OF THE INVENTION

1. Field of the Invention

The apparatus of the present invention relates to catheter fluid-velocity flow probes of the electromagnetic type, all of which may be referred to as flow probes.

2. Description of the Prior Art

In recent years there has been much research and development in the art of catheter devices suitable for insertion into the body of a human or animal subject to measure various functions of body fluids. For example, in U.S. Pat. Nos. 3,724,274 and 3,748,623 to Millar there are disclosed pressure transducers suitable for attachment to a catheter for implantation into an artery or vein to measure the blood pressure of a person at a given point.

In U.S. Pat. No. 3,516,399 to Barefoot there is disclosed an electromagnetic catheter blood flow probe suitable for attachment to the distal end of a catheter. When the catheter containing the blood flow probe is inserted into an artery or vein, velocity of blood in that artery or vein may be measured.

The blood flow probe disclosed by Barefoot comprises an electromagnet consisting of a U-shaped iron core onto which is wound a suitable number of turns of wire. When a voltage is applied between the ends of the wire, a magnetic field is created between the open ends of the U-shaped iron core. Electrodes are disposed within the magnetic field that is created in the probe tip, and, when blood flow past these electrodes, a voltage is induced across them. Conductors connect the electrodes to a connector attached to the proximal end of the catheter.

The voltage induced across the electrodes is directly proportional to the number of magnetic flux lines that the blood is able to intersect as it flows by the probe. It is known that the number of magnetic flux lines emerging from the electromagnet may be increased by increasing the number of turns of wire on the iron core. As the number of turns of wire on the iron core is increased, however, the electrical resistance of the electromagnet increases. Consequently, the amount of heat generated in the probe increases. It should be apparent that an excessive amount of heat dissipated at the probe tip can cause damage to a blood vessel or to the blood.

It would be desirable to construct a multi-function catheter probe so that multiple measurements and/or samples could be taken with a single catheterization. For example, it might be desirable to have a catheter having both a flow probe and a pressure transducer attached to the distal end of the catheter. One such flow probe is the one shown in an article entitled "Sensitivity of Electromagnetic Velocity Probes", Phys. Med. Biol., Vol. 16, No. 2, pp. 229-232 (1971). This flow probe employs a coil without a ferromagnetic core. Since there is no ferromagnetic core, sufficient cross-sectional area is available in the probe to provide a central lumen. The proximal end of the lumen in the flow probe may be attached to the distal end of the catheter, and a suitable pressure transducer may be attached to the lumen at the distal end of the probe.

It has been found that the flow probe described in the preceeding paragraph: (1) becomes very hot in operation; and (2) lacks sufficient sensitivity for reliable measurements. Both problems are believed to be directly attributable to the coil requirements in the absence of a ferromagnetic core.

The Carolina-Millar catheter, which employed multiple measurement devices attached to its distal end, is shown and discussed in Review of Surgery, Vol. 29, No. 2, p. 149, Mar.-Apr. 1972. The measurement devices employed were the blood flow probe with a ferromagnetic core disclosed by Barefoot in U.S. Pat. No. 3,516,399 and the pressure transducer disclosed in U.S. Pat. No. 3,724,274 to Millar. In this device a passage for wires was provided between the proximal end of the catheter and the pressure transducer at the distal tip.

The size of the core of the electromagnet in the Carolina-Millar catheter was substantially reduced to provide sufficient cross-sectional area for the passage of wires to the pressure transducer, and a reduction of the sensitivity of the blood flow probe was observed. In other words, the performance of prior art flow probes with ferromagnetic cores deteriorated when a passage was provided for the attachment of multiple measurement devices to the distal end of the probe.

Accordingly, it is an objective of this invention to provide a catheter fluid-velocity flow probe which is adaptable to have other attachments added thereto without reducing probe sensitivity. Such attachments may include, for example, a pressure tranducer attachment, a fiber optic attachment, or a blood sample gathering attachment.

Furthermore, it is another objective of the present invention to provide a catheter fluid-velocity flow probe which has greater sensitivity and dissipates less heat in operation than do blood flow probes of the prior art.

SUMMARY OF THE INVENTION

The catheter fluid-velocity flow probe according to the present invention has sensitivity greater than the sensitivity of flow probes of the prior art and generates less heat in operation than do the flow probes of the prior art. Furthermore, the flow probe of the present invention provides for the attachment of additional measuring devices to the distal end of the probe and passage of communicating wires through the probe without reducing the sensitivity of the probe. These advantages are realized by the manner in which the electromagnets are constructed and by the location of the electrodes in the probe with respect to the electromagnets.

In its broadest aspects, the catheter fluid-velocity flow probe of the present invention comprises a housing and two electromagnets disposed in the housing for generating two separate magnetic fields. Each electromagnet comprises a ferromagnetic core having two poles, and each core is formed into a suitable configuration. An electrical conductor is wound to form a coil on ech ferromagnetic core. The electromagnets so formed are disposed in the probe with the poles of each in proximity to the exterior of the probe. Two electrodes are located in the housing with exposed outer surfaces for fluid-electrode interface, each electrode being disposed such that the exposed outer surface for the fluid-electrode interface is substantially between the poles of the respective electromagnets. A conductor is provided to each electrode to provide electrical continuity between the electrode and the proximal end of the catheter. Electrically insulating bonding material is used to encapsulate the housing of the probe, and the bonding material is formed to permit exposure of the outer surfaces of the electrodes. Fluid flowing past the probe will come into direct contact with the electrodes, and a voltage will be induced across them by the flow, which voltage may be measured with a suitable measuring device at the proximal end of the catheter.

A tubing may be inserted in the probe during construction to add structural strength to the probe and to permit a continuous lumen between the proximal and distal ends of the probe. The part of the lumen at the proximal end of the probe may be coupled to the distal end of a catheter having a central lumen. Additional measuring devices, e.g., a pressure transducer, may be coupled to the portion of the lumen at the distal end of the probe with the communicating conductors passing through the tubing and to the proximal end of the catheter.

In one embodiment of the apparatus of the present invention, each of two electromagnets comprises a ferromagnetic core which is formed into a generally U-shaped configuration. An electrical conductor is wound to form a coil on each U-shaped core in an identical manner. Each electromagnet is disposed in proximity to the exterior of the probe in a plane substantially parallel to the longitudinal axis of the probe and in spaced relationship with the other electromagnet so formed. An electrode is disposed substantially between the poles of each electromagnet so as to be located in the region of highest magnetic flux density. The probe is encapsulated with electrically insulating bonding material to form the probe housing. The housing of the probe is formed to permit exposure of each electrode so that fluid flowing past the electrodes will come into direct contact with them. Voltages are induced across the electrodes by the movement of the fluid through the magnetic fields.

In another embodiment of the present invention, each of two electromagnets comprises a ferromagnetic core which is formed into a substantially toric configuration with a gap between the two ends of the core. The portions of the toric core on either side of the gap are the poles of each electromagnet. An electrical conductor is wound to form a coil on each toric ferromagnetic core in an identical manner. Each electromagnet is disposed in the probe in a plane substantially perpendicular to the longitudinal axis of the probe and in spaced relationship with the other electromagnet with gaps preferably disposed on opposite sides of the probe. An electrode is positioned between the poles of each electromagnet, in the region of highest magnetic flux density of the magnetic field that is created by each eletromagnet. The probe is encapsulated with electrically insulating bonding material to form the probe housing. The electrically insulating bonding material is formed to permit exposure of the electrodes so that fluid flowing past the electrodes will come into direct contact with them. A central tubing may be inserted through the toric electromagnets, thereby enabling the attachment of additional devices to the distal end of the probe in the manner described above. The ends of each core may be extended in a plane which is substantially parallel to the longitudinal axis of the probe.

In another embodiment of the present invention, an electrical conductor is wound to form identical coils on each of two U-shaped ferromagnetic cores to form two electromagnets. Each electromagnet is formed into a generally helical configuration about the longitudinal axis of the probe. This embodiment permits the construction of an electromagnet with a gap having a relatively higher magnetic flux density per unit length of probe.

In another embodiment of the present invention, each of two electromagnets comprises a ferromagnetic core which is formed into a generally toric configuration with a gap between the two ends of the core. The portions of the toric core on either side of the gap are the poles of each electromagnet. An electrical conductor is wound to form identical coils on each toric ferromagnetic core. Each electromagnet is disposed in the probe in a plane which forms an angle with the longitudinal axis of the probe and in spaced relationship with the other electromagnet with gaps preferably disposed on opposite sides of the probe. The ends of each core may be extended in a plane which is substantially parallel to the longitudinal axis of the probe. An electrode is positioned between the poles of each electromagnet. The probe is encapsulated with electrically insulating bonding material to form the probe housing. The electrically insulating bonding material is formed to permit exposure of the electrodes so that fluid flowing past the electrodes will come into direct contact with them. A central tubing may be inserted through the toric electromagnets, thereby enabling the attachment of additional devices to the distal end of the probe in the manner described above.

In each of the preceeding embodiments of the invention the ferromagnetic cores of the electromagnets are not in direct contact with each other. An electrical conductor may be wound to form a coil on each core in an identical manner, with the start winding near the first pole of the electromagnet and with the stop winding near the second pole of the electromagnet. An electrical conductor may be used to connect the stop winding on the first core with the start winding on the second core, thereby providing electrical continuity between the start winding on the first core and the stop winding on the second core. A center-tap conductor is electrically connected to the electrical connection between the stop winding on the first core and the start winding on the second core.

In yet another embodiment of the present invention, two electromagnets are constructed by winding an electrical conductor to form a single coil on two adjoined generally U-shaped ferromagnetic cores. The closed ends of the U-shaped ferromagnetic cores are spread apart to allow the insertion of a central tubing member through the middle of them. The open ends of the U-shaped ferromagnetic cores are spread apart and formed so as to provide two separate regions of magnetic flux on opposite sides of the probe. The electrodes are again placed between the poles of the electromagnets in the regions of highest magnetic flux density.

In yet another embodiment of the present invention, only one electromagnet is utilized which comprises a ferromagnetic core which is formed into a generally toric configuration with a gap between the two ends of the core. The portions of the toric core on either side of the gap are the poles of the electromagnet. An electrical conductor is wound to form a coil on the toric ferromagnetic core. The electromagnet is disposed in the probe in a plane which forms an angle with the longitudinal axis of the probe. The ends of the core may be extended in a plane which is substantially parallel to the longitudinal axis of the probe. An electrode is positioned between the poles of the electromagnet, and a neutral reference electrode is positioned in the probe; e.g., an electrode that does not have an electromagnet associated with it. The probe is encapsulated with electrically insulating bonding material to form the probe housing. The electrically insulating bonding material is formed to permit exposure of the electrodes so that fluid flowing past the electrodes will come into direct contact with them. A central tubing may be inserted through the toric electromagnet, thereby enabling the attachment of additional devices to the distal end of the probe in the manner described above.

In another embodiment of the present invention, only one electromagnet is utilized which comprises a ferromagnetic core which is formed into a generally toric configuration with a gap between the two ends of the core. The portions of the toric core on either side of the gap are the poles of the electromagnet. An electrical conductor is wound to form a coil on the toric ferromagnetic core. The electromagnet is disposed in the probe in a plane which is substantially perpendicular to the longitudinal axis of the probe. The ends of the core may be extended in a plane which is substantially parallel to the longitudinal axis of the probe. An electrode is positioned between the poles of the electromagnet, and a neutral reference electrode is positioned in the probe; e.g., an electrode that does not have an electromagnet associated with it. The probe is encapsulated with electrically insulating bonding material to form the probe housing. The electrically insulating bonding material is formed to permit exposure of the electrodes so that fluid flowing past the electrodes will come into direct contact with them. A central tubing may be inserted through the toric electromagnet thereby enabling the attachment of additional devices to the distal end of the probe in the manner described above.

BRIEF DESCRIPTION OF THE DRAWINGS

In the accompanying drawings:

FIG. 1 is the front view of a person which illustrates a catheter device inserted into a person;

FIG. 2 is an isometric view of a flow probe constructed in accordance with the prior art;

FIG. 2A is a cross-sectional view of the flow probe shown in FIG. 2 taken along line 2A—2A of FIG. 2;

FIG. 3 is an isometric view of an embodiment of the present invention which illustrates multiple measuring devices attached to the distal end of a catheter;

FIG. 4 is an isometric view of the interior portion of one embodiment of the flow probe of the present invention;

FIG. 5 is an isometric view of an encapsulated embodiment of the flow probe shown in FIG. 4;

FIG. 6 is a cross-sectional view of the embodiment of FIG. 5 taken along line 6—6 of FIG. 5;

FIG. 7 is a cross-sectional view of the embodiment of FIG. 5 taken along line 7—7 of FIG. 5;

FIG. 8 is a cross-sectional view of the embodiment of FIG. 5 taken along line 8—8 of FIG. 7;

FIG. 9 is a longitudinal cross-sectional view of an embodiment of the present invention which illustrates the coupling for additional devices to the distal end of the flow probe;

FIG. 15 is an isometric view of yet another embodiment of the flow probe of the present invention;

FIG. 16 is a cross-sectional view taken along line 16—16 of FIG. 15;

FIG. 17 is an isometric view of the exterior of the embodiment of the invention shown in FIG. 15 after encapsulation;

FIG. 18 is a cross-sectional view taken along line 18—18 of FIG. 17;

FIG. 19 is a longitudinal cross-sectional view of the device of FIG. 15 which illustrates the manner in which the distal end of an embodiment of the flow probe of the present invention may be encapsulated;

DESCRIPTION OF THE PREFERRED EMBODIMENTS

Figure 10:
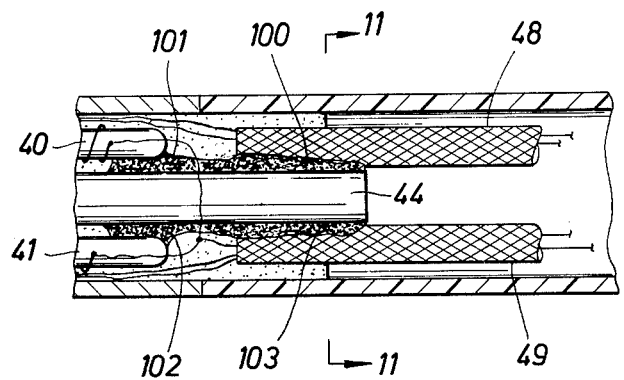
FIG. 10 is a longitudinal cross-sectional view of an embodiment of the present invention which illustrates the manner in which electrical conductors may be shielded.
Figure 11:
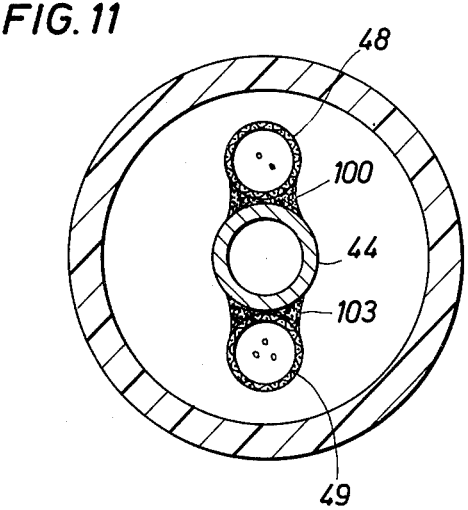
FIG. 11 is a cross-sectional view of the embodiment of FIG. 10 taken along line 11—11 of FIG. 10.

It will be appreciated that the present invention can take many forms and embodiments. A limited number of the embodiments of the invention will be presented so as to give an understanding of the invention. It is not intended, however, that the limited embodiments herein set forth should in any way limit the invention.

Referring now to FIG. 1, a catheter 29 is a medical device which may be inserted into a fluid-carrying vessel of a person or animal ("the subject") to make specified measurements in the fluid in that vessel or to withdraw a sample of fluid from that vessel. The type of measurement that is made with the catheter is determined by the type of attachment which is coupled to catheter 29. When a measuring device is attached to the distal end 29a, a connector 29c is coupled to the proximal end 29b of the catheter for connection to suitable measuring equipment (not shown). As previously mentioned, a variety of devices suitable for attachment to the distal end of a catheter have been developed in recent years.

Before the description of the fluid velocity probes of the present invention and of the prior art are discussed, it is appropriate to include a brief discussion of the general theory of operation of flow probes. It is wellknown that a voltage is induced in a conductor whenever the conductor is moved through a magnetic field in a direction so as to intersect lines of magnetic flux, and conversely, the same phenomenon occurs when the magnetic field is moved similarly across a conductor. It is this relative motion between magnetic field and conductor that induces a voltage in the conductor. The fluid that is moving in the vessel of the subject into which a flow probe is inserted can be thought of as a continuous conductor. Thus, measurement of the fluid velocity depends upon the induction of voltage in the fluid flowing through a magnetic field, and the voltage will be induced at right angles to the direction of motion of the fluid and to the magnetic field. The polarity of the induced voltage depends upon the polarity of the magnetic field and the direction of motion of the fluid. The magnitude of the induced voltage is determined by the velocity of the fluid and the strength of the magnetic field, and, when fluid velocity and vessel size are known, fluid flow rate calculations can be read directly from calibrated equipment.

With reference now to FIG. 2, there is shown a flow probe 25 according to the prior art. Flow probe 25 may be attached to the distal end 29a of catheter 29 (FIG. 1) to measure the velocity of blood in an artery or vein. It will be helpful to understand the manner in which this flow probe operates in order to appreciate fully the significance of the flow probe of the present invention.

Still referring to FIG. 2, the flow probe 25 according to the prior art comprises a U-shaped iron core 31 onto which wire 33 is wound to form an electromagnet. When a voltage 34 is applied between the ends of wire 33, a magnetic field is created. Lines of magnetic flux, which are indicated in FIG. 2A by dashed lines, exist between the poles 31a and 31b of the electromagnet, and the lines of magnetic flux are most dense in the gap directly between poles 31a and 31b of the electromagnet. Electrodes 36 and 37 are positioned on the exterior of the flow probe as illustrated in FIG. 2A.

It will be observed from the flow probe shown in FIGS. 2 and 2A that the electrodes 36 and 37 sre not positioned in the region of highest magnetic flux density. Rather, they are positioned in the fringe areas of the magnetic field created by the electromagnet. Voltages which are induced across electrodes 36 and 37 by a given velocity of fluid flow are, therefore, less than voltages which would be induced if the electrodes 36 and 37 were positioned in a region of higher magnetic flux density.

Referring again to FIGS. 2 and 2A, in order for voltages of sufficient magnitude for acceptable measurements to be induced across electrodes 36 and 37 of flow probe 25, it is necessary for the size of iron core 31 to be substantial and for many turns of wire 33 to be wound upon it. This being the case, flow probe 25 is not adaptable to having other operational devices attached distally to it in a catheter of a physiologically practical size, because the electromagnet and electrodes occupy substantially all of the cross-sectional area of probe 25.

As previously noted, flow probes have been developed which permitted additional devices to be attached to their distal ends. In order to provide a passageway in flow probe 25, the size of iron core 31 or the amount of wire 33 had to be substantially reduced. This reduction resulted in lower voltages being induced across electrodes 36 and 37 during operation because a lower intensity magnetic field was generated in the probe. Hence, the performance of a flow probe with a ferromagnetic core of the prior art deteriorated when such a probe was constructed to permit additional measuring devices to be attached to its distal end.

The broadest aspects of the invention will be described with respect to the embodiment of the invention shown in FIG. 4. It will be appreciated that other embodiments of the invention could be utilized to make this description.

Referring now to FIG. 4, a flow probe 75 constructed in accordance with an embodiment of the present invention comprises two electromagnets 101 and 102 to generate two separate magnetic fields. Each electromagnet 101 and 102 has a ferromagnetic core, 40 and 41, respectively, and each ferromagnetic core 40 and 41 has a gap between respective magnetic poles. The electromagnets 101 and 102 are disposed in the housing of the probe. Each electrode 42 and 43 is disposed such that the exposed surface for fluid-electrode interface is substantially in the gap between the poles of each electromagnet 101 and 102, respectively.

With reference to FIGS. 4, 5 and 6, the electromagnets 101 and 102 and electrodes 42 and 43 may be encapsulated with electrically insulating bonding material 81. Bonding material 81 is formed with an indentation in the exterior surfaces or otherwise to permit the exposure of the outer surfaces of electrodes 42 and 43 as a fluid-electrode interface. When a conductive fluid flows past the fluid-electrode interface of electrodes 42 and 43, a voltage will be induced across the electrodes. The magnitude of the induced voltage is directly proportional to the velocity with which the fluid flows past electrodes 42 and 43 and upon the magnetic flux density in the region of flow near the electrodes 42 and 43.

Disposing the electrodes substantially in the gap of each core results in each electrode being in a region of higher magnetic flux density than were electrodes in prior art flow probes. The result of this positioning is that a voltage is induced across the electrodes which is greater than the voltage which would be induced if the electrodes were located in the fringe area of the magnetic field for a given fluid flow velocity past the electrodes. Furthermore, the positioning of the electrodes between the poles of the electromagnets permits the electromagnets which are utilized to be smaller in size than the electromagnets utilized in flow probes of the prior art. Consequently, less wire is required to fabricate the electromagnets, resulting in less heat generation in the flow probe during operation. The performance of a flow probe constructed in accordance with the present invention is set forth below following the description of its various embodiments.

A special feature of the flow probe according to the present invention enables one or more communicating channels to be provided through the length of the probe for communication by such means as the passage of wires, optic fibers, or fluids. For example, referring to FIG. 4, a single tube 44 is shown for such communication. FIG. 3 illustrates a catheter having multiple sensors attached distally, with two such communicating channels for isolated passage of wires through the probe.

With reference now to FIG. 4, there is shown a view of one embodiment of a flow probe constructed in accordance with the present invention. It comprises two ferromagnetic cores, 40 and 41, onto which wire 45 is wound to form two electromagnets 101 and 102, respectively. Ferromagnetic cores 40 and 41 may, for example, be made of iron. Each core 40 and 41 is formed into a generally U-shaped configuration.

With reference still to FIG. 4, the electromagnets 101 and 102 are preferably disposed in the probe in a plane substantially parallel to the longitudinal axis of the probe and in spaced relationship with each other. Electrodes 42 and 43 are disposed substantially in the gap between the poles of the electromagnets, and electrodes 42 and 43 are preferably made of silver or platinum. Wires are connected to the electrodes 42 and 43 for connection between the electrodes and the connector at the proximal end of the catheter. The U-shaped members 40 and 41 and the electrodes 42 and 43 may be suitably bonded to the central tubing 44 by epoxy or other electrically insulating bonding material.

Figure 12:
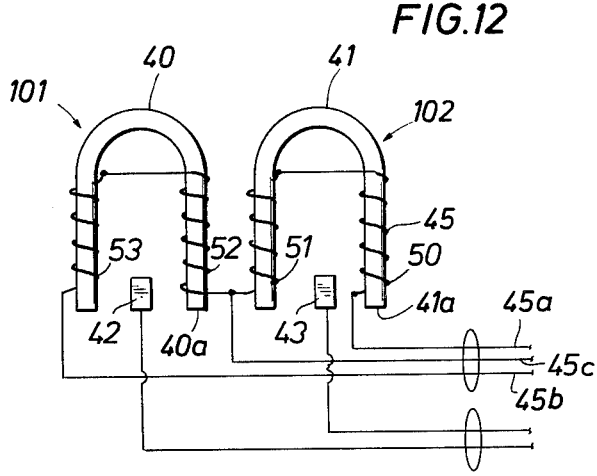
FIG. 12 is an electrical schematic diagram which illustrates the manner in which the electromagnets and electrodes which are used in some embodiments of the present invention are electrically connected.

Referring now to FIG. 12, an electrical conductor 45 is wound to form a coil on each ferromagnetic core 40 and 41 in an identical manner. The windings begin (start winding 50 and 52) on one side of the gap and terminate (stop windings 51 and 53) on the other side of the gap. A conductor is provided between stop winding 51 and start winding 52, thereby providing electrical continuity between start winding 50 of electromagnet 102 and stop winding 53 of electromagnet 101.

Referring now to both FIGS. 4 and 12, when a voltage is applied between the ends 45a and 45b of conductor 45 (FIG. 12), ends 40a and 41a of ferromagnetic cores 40 and 41 will both be north or both be south poles of the electromagnets. Fluid flowing past electrodes 42 and 43 (FIGS. 4 and 5) in a direction along the longitudinal axis of the probe will induce a positive voltage at one electrode and a negative voltage at the other electrode. The electronic equipment (not shown) that is coupled to the proximal end 29b of catheter 29 (FIG. 1) may be arranged to measure the difference of the voltages induced at the electrodes. Since the induced voltages will have opposite polarities, their difference will be a voltage having a magnitude equal to the sum of the absolute values of each voltage.

It is quite commonplace for the flow probe to come into contact with the wall of the vessel into which it is inserted. When this occurs, the probe may be oriented in the vessel such that one of the electrodes is in contact with the wall of the vessel. In this situation, the fluid velocity past the electrode which is in contact with the vessel wall will decrease, and the magnitude of the voltage which is induced across the electrodes will, therefore, decrease. When the magnitude of the induced voltage decreases, it is desirable to know if the flow probe is in contact with the vessel wall or if the velocity of the fluid in the vessel has actually decreased.

Still referring to FIG. 12, center-tap conductor 45c is connected to the electrical conductor between stop winding 51 of electromagnet 102 and start winding 52 of electromagnet 101. When a decrease in voltage across the electrodes 42 and 43 is observed, the voltage that was applied between ends 45a and 45b may be first applied between 45c and 45a and then between 45c and 45b. During each application of the driving voltage, only one electromagnet 102 or 101 is energized. If one electrode 42 or 43 is in contact with the vessel wall or is in contact with a flow obstruction, then a substantial difference between induced voltage levels at each electrode will be observed. Alternatively, the direction of current can be reversed in one electromagnet only, by applying the driving voltage between conductor 45c and conductors 45a and 45b. If the fluid velocity past each electrode is identical, then the total probe output will approximate zero volts. If, however, the flow of fluid past one electrode is obstructed, then the difference output from the probe will not approximate zero volts and the position of the probe may be changed accordingly.

Referring now to FIG. 5, there is shown the manner in which the embodiment of the invention shown in FIG. 4 is encapsulated. Tubing 55 is used to encase the electromagnets 101 and 102 and central tubing 44 shown in FIG. 4. Tubings 44 and 55 may, for example, be stainless steel. The outer diameter of tubing 55 should correspond to the outer diameter of the catheter, and portions of the cylindrical surface area of tubing 55 are removed to provide slots in the tube wall. The flow probe may be encapsulated with suitable material 81, e.g., epoxy, and this filler material 81 is indented from the slots in the tube wall of tubing 55 to the outer surfaces of electrodes 42 and 43. The outer surfaces of electrodes 42 and 43 are therefore exposed as fluid-electrode interfaces, and, when the catheter is inserted into a fluid-carrying vessel, electrodes 42 and 43 will come in direct contact with the fluid flowing past them. The depth of the indentation is naturally dependent upon the location of the electrodes within the probe. However, the indentation must not be of such a depth whereby, in the measurement of velocity in blood, blood could readily accumulate and clot, thus impeding the operation of the electrode and flow probe.

With reference again to FIGS. 1 and 4, when the flow probe is coupled to the distal end 29a of catheter 29, conductors provide the electrical continuity between both the electrodes 42 and 43 and the electromagnets 101 and 102 in the probe and the connector 29c at the proximal end 29b of catheter 29. Since the signal voltage, which is induced across electrodes 42 and 43 when the flow probe is in place in a subject, is quite low as compared to the voltage applied to the electromagnets, it is desirable to provide as much electrical shielding as possible for the conductors to the electrodes. This shielding is accomplished in one embodiment of the flow probe of the present invention by providing braided shield 48 into which the conductors from the electrodes 42 and 43 are inserted and shield 49 into which the conductors from the electromagnets 101 and 102 are inserted. Braided shields 48 and 49 provide shielding for the conductors between the distal end 29a and the proximal end 29b of catheter 29. Of course, other materials which have suitable electrical shielding characteristics may be utilized for shields 48 and 49.

It has been stated that it is an objective of the present invention to provide a flow probe which allows additional measuring devices to be attached distal to the probe at the distal end of the catheter, but which does not sacrifice probe sensitivity by so doing. As below discussed, these measuring attachments may be transducers whose conductor wires travel from the distal end 29a of catheter 29 to the proximal end 29b of catheter 29 via central tubing 44. In other words, central tubing 44 is a conduit for these conductor wires. Since the signal picked up by these measuring devices may be small as compared to the voltage applied to the electromagnets, it is desirable to minimize interference by shielding either the conductors to the distal measuring devices or the conductors to the electromagnets. It has been found to be preferable to shield the conductors to the electromagnets, and shielding along the length of the catheter is provided for the conductors to the electromagnets by shield 49.

With reference now to FIG. 10, there is shown a longitudinal cross-sectional view of the embodiment of the flow probe shown in FIG. 4. FIG. 10 more clearly shows the arrangement of the shields 48 and 49 with respect to the electromagnets. It has been found through experience with prior art flow probes that a physiologically significant amount of heat is generated during operation. This being the case, shields 48 and 49 and U-shaped ferromagnetic cores 40 and 41 are soldered or otherwise thermally bonded to central tubing 44 as shown in FIG. 10. The bonded connections of these elements are shown by reference numerals 100–103. This thermal bonding technique allows a large amount of the heat which would otherwise be dissipated in a subject during the operation of the flow probe to be dissipated through the central tubing 44 and along the catheter through the shielding. In other words, central tubing 44 and the attached shields serve as a heat sink for heat generated in the probe.

Figure 13:
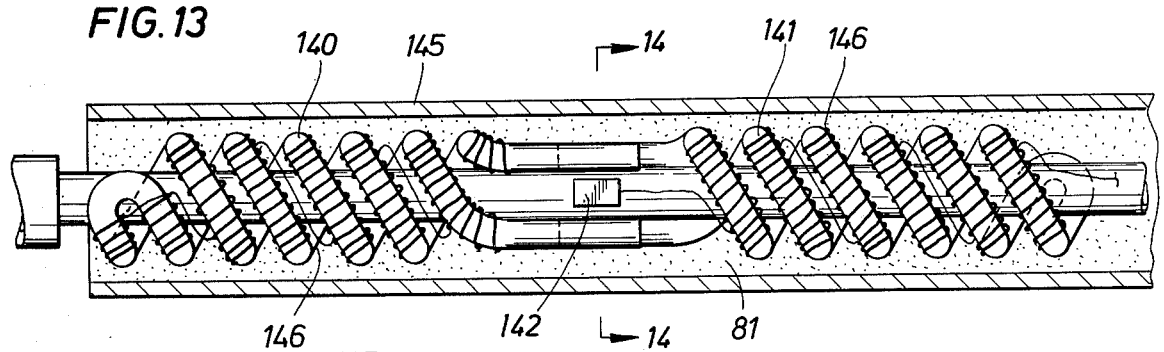
FIG. 13 is a longitudinal cross-sectional view of another embodiment of the present invention.

With reference now to FIG. 13, there is shown another embodiment of a flow probe constructed in accordance with the present invention. In this embodiment, each ferromagnetic member 140 and 141 is formed into a generally U-shaped configuration and wire 146 is wound on each to form a coil. The winding of members 140 and 141 is preferably accomplished in the same manner as shown in FIG. 12. Each member is then twisted in a generally helical configuration shown in FIG. 13 about the longitudinal axis of the probe. The helical configuration into which members 140 and 141 are twisted permits a greater number of windings per unit length of flow probe. Consequently, members 140 and 141 can initially be equal in length to members 40 and 41 (FIG. 4), but can fit into a shorter length of probe than can members 40 and 41. The greater number of windings per unit length obtained with the embodiment of the invention shown in FIG. 13 results in an equivalent magnetic flux density being generated by this embodiment with a significant reduction in probe length.

Figure 14:
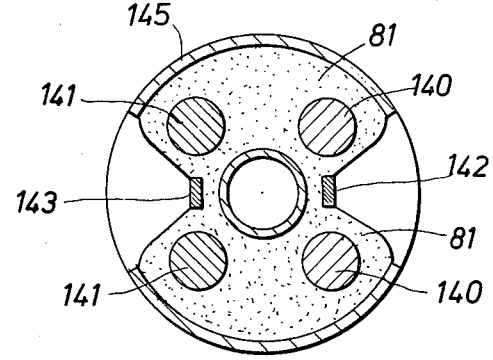
FIG. 14 is a cross-sectional view taken along line 14—14 of FIG. 13.

With reference to FIG. 14, electrodes 142 and 143 are disposed in the gaps between the poles of members 140 and 141. This is the region of highest magnetic flux density and FIG. 14 shows this positioning most clearly. Tubing 145 is used to encase the electromagnets and electrodes. Tubing 145 is slotted in the regions of the electrodes 142 and 143. Suitable electrically insulating material 81, such as epoxy, is used to encapsulate the flow probe, and material 81 is formed to permit exposure of electrodes 142 and 143 as previously described.

With reference now to FIGS. 15–19, there is shown another embodiment of a flow probe constructed in accordance with the present invention. In this embodiment, the electromagnets comprise ferromagnetic cores 150 and 151, onto which conductor 156 is wound in the manner shown in FIG. 12. Ferromagnetic cores 150 and 151 are each formed in a generally toric configuration with a gap between the ends 150a and 150b and ends 151a and 151b of each member. The poles of each electromagnet are the portions of the ferromagnetic core on either side of the gap. Each electrode 152 and 153 is disposed such that the exposed surface for the fluid-electrode interface is substantially in the gap between the poles of ferromagnetic cores 150 and 151.

With reference now to FIG. 16, there is shown a cross-sectional view of the device of FIG. 15 which illustrates the location of electrode 153 between the poles of the electromagnet comprising toric member 151. As with the previous embodiments, the placement of the electrodes between the poles of each electromagnet results in the electrodes being in the region of highest magnetic flux density of each electromagnet.

Referring to both FIGS. 1 and 15, shield 157 (FIG. 15) is provided in the flow probe and in the catheter 29 (FIG. 1) from its proximal end 29b to its distal end 29a. Conductors 158 and 159, which connect the electrodes 152 and 153 to connector 29c at the proximal end 29b of the catheter 29, are inserted between tubing 44 and shield 157. Conductors 156, which are wound on members 150 and 151, extend from the probe to connector 29c at the proximal end 29b (FIG. 1) of catheter 29 along the surface of shield 157 that is nearest the catheter wall. Shield 157 performs essentially the same functions as shields 48 and 49 of FIGS. 4 and 10.

With reference now to FIG. 17, the flow probe of FIG. 15 is encased by positioning tubing 170 over the electromagnets and electrodes shown in FIG. 15. Tubing 170 contains cutout portions 171 and 172. Suitable electrically insulating material 173, such as epoxy, may be utilized to encapsulate the flow probe. Material 173 is again formed to permit direct exposure of electrodes 152 and 153, as previously described, to enable fluid to come into contact with them when the probe is inserted in a fluid-carrying vessel.

Figure 20:
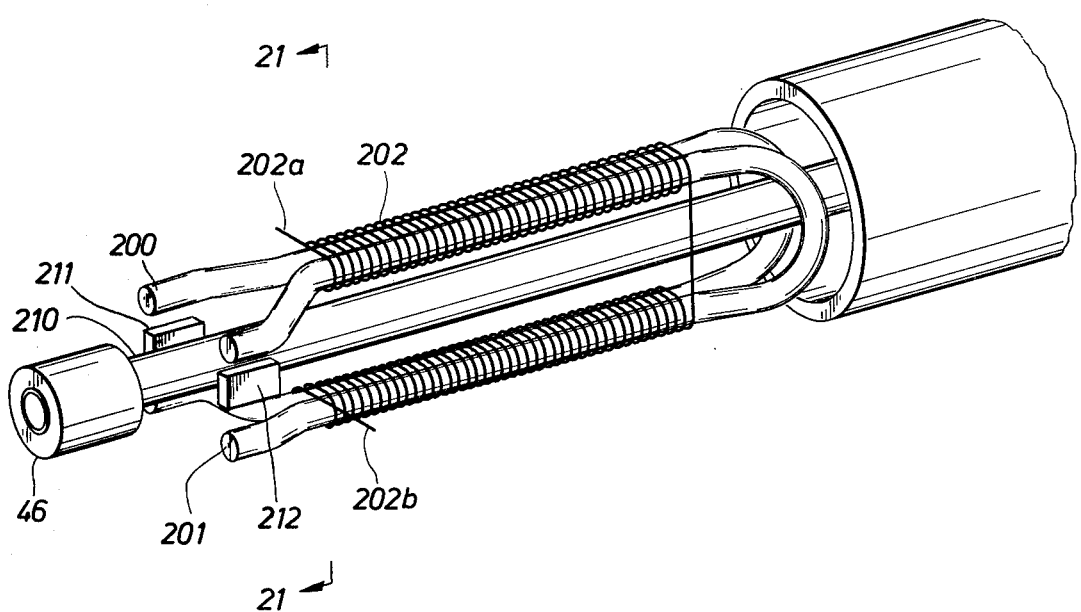
FIG. 20 is an isometric view of another embodiment of a flow probe constructed in accordance with the present invention.
Figure 21:
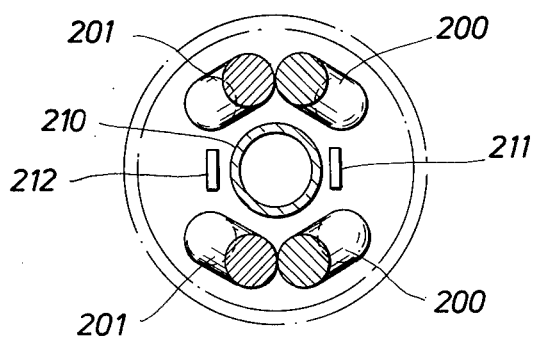
FIG. 21 is a cross-sectional view taken along line 21—21 of FIG. 20.

With reference now to FIG. 20, there is shown another embodiment of a flow probe constructed in accordance with the present invention. It comprises ferromagnetic cores 200 and 201, which are each formed in a generally U-shaped configuration. Ferromagnetic cores 200 and 201 are placed in contact with each other and both are encompassed by each winding of conductor 202. The open ends (poles) of U-shaped members 200 and 201 are spread apart as shown in FIG. 20 to form two electromagnets. When the electromagnets are disposed in the probe, two separate regions for magnetic flux are provided on opposite sides of the probe. When a voltage is applied between the ends 202a and 202b of conductor 202, both electromagnets are activated. This embodiment utilizes less wire than the embodiment of FIG. 4, for example, and consequently, has less electrical resistance in the electromagnets than does the embodiment of FIG. 4. This being the case, less heat is generated with the embodiment of FIG. 20 than with the embodiment of FIG. 4. The arcuate ends of U-shaped ferromagnetic core 200 and 201 may be spread apart as shown in FIG. 20 to allow the insertion of metal tubing 210 between them.

Electrodes 211 and 212 are again placed between the poles of the respective electromagnets as previously described. As aforementioned, this placement is made so that the electrodes 211 and 212 will be in the regions of highest magnetic flux density of the electromagnets.

The embodiment of the present invention shown in FIG. 20 has a disadvantage that the other embodiments heretofore shown do not have. The windings on the electromagnets which are used in the embodiments of the invention shown in FIG. 4, 13, and 15 are preferably wound in the manner shown in FIG. 12. Since the ferromagnetic cores 200 and 201 are magnetized by the same coil, the ferromagnetic cores 200 and 201 may not be independently magnetized as in the other embodiments of the invention heretofore shown and discussed. This being the case, a difference in fluid velocity caused by obstruction to flow at either electrode cannot be readily identified.

Figure 22:
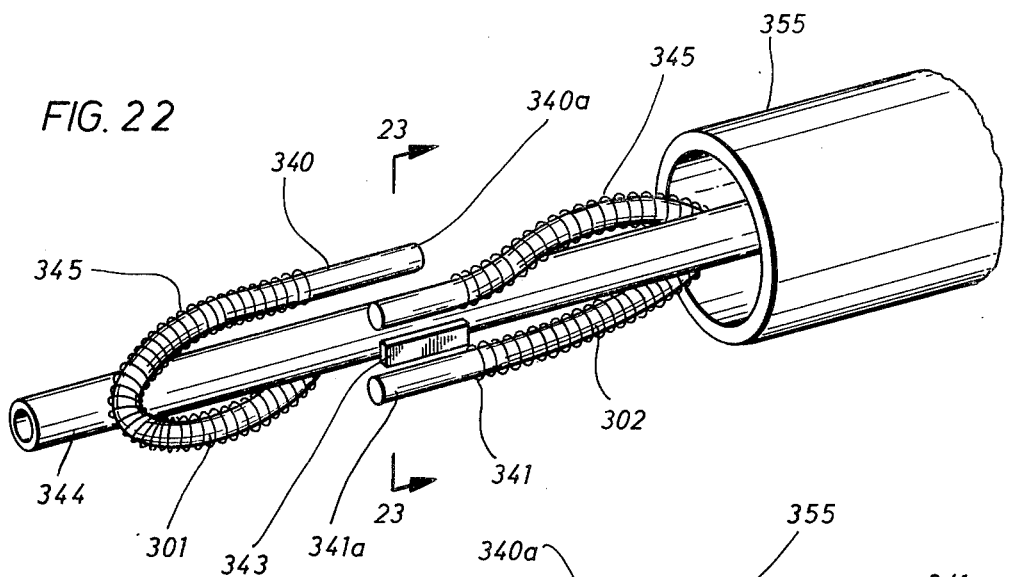
FIG. 22 is an isometric view of the interior portion of one embodiment of the flow probe of the present invention.

With reference now to FIG. 22, there is shown a view of another embodiment of a flow probe constructed in accordance with the present invention. It comprises two ferromagnetic cores, 340 and 341, onto which wire 345 is wound to form two electromagnets 301 and 302, respectively. Ferromagnetic cores 340 and 341 may, for example, be made of iron. Each core 340 and 341 is formed into a generally toric configuration.

Figure 24:
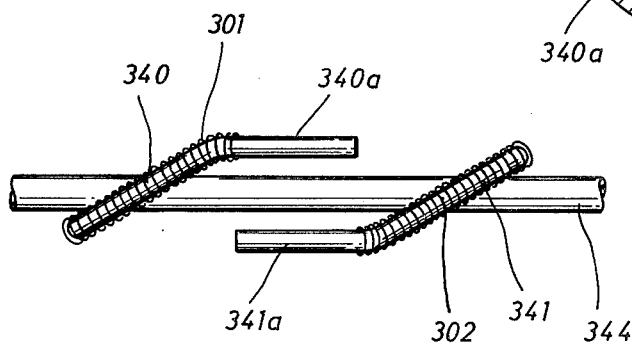
FIG. 24 is a plan view of the embodiment of FIG. 22.

With reference to FIG. 24, the electromagnets 301 and 302 are preferably disposed in the probe in a plane which forms an angle with the longitudinal axis of the probe. The ends 340a and 341a of ferromagnetic cores 340 and 341 are extended in a plane which is substantially parallel to the longitudinal axis of the probe, thereby establishing the poles of the electromagnets 301 and 302.

Figure 23:
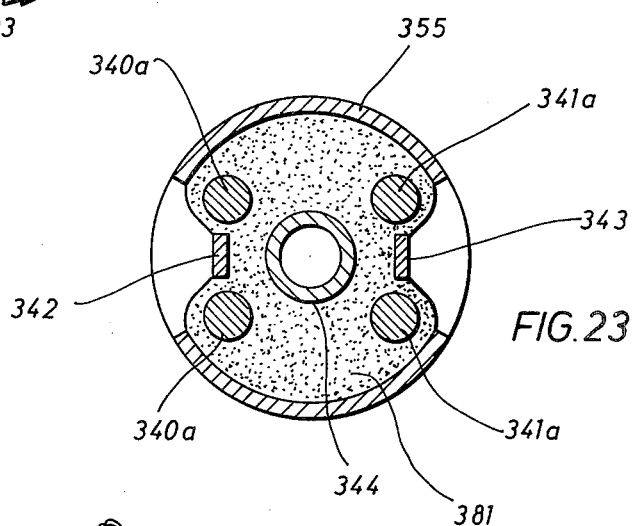
FIG. 23 is a cross-sectional view of the embodiment of FIG. 22 taken along line 23—23 of FIG. 22.

As shown in FIGS. 22 and 23, electrodes 342 and 343 are disposed substantially in the gap between the poles of the electromagnets 301 and 302. Electrodes 342 and 343 are preferably made of silver or platinum. As previously described, a communicating channel, or tube, 344 is provided through the length of the probe for communication by such means as the passage of wires, optic fibers, or fluids. The toric members 340 and 341 and the electrodes 342 and 343 may be suitably bonded to the central tubing 344 by epoxy or other electrically insulating bonding material.

Referring now to FIG. 23, there is shown the manner in which the embodiment of the invention shown in FIG. 22 is encapsulated. Tubing 355 is used to encase the electromagnets 301 and 302 and central tubing 344. Tubings 344 and 355 may, for example, be stainless steel. The outer diameter of tubing 355 should correspond to the outer diameter of the catheter, and portions of the cylindrical surface area of tubing 355 are removed to provide slots in the tube wall adjacent the location of electrodes 342 and 343. The encased flow probe may be encapsulated with suitable material 381, e.g., epoxy, and this filler material 381 is indented at the slots in the tube wall of tubing 355 to expose the outer surfaces of electrodes 342 and 343. The outer surfaces of electrodes 342 and 343 are therefore exposed as fluid-electrode interfaces, and, when the catheter is inserted into a fluid-carrying vessel, electrodes 342 and 343 will come in direct contact with the fluid flowing past them.

The embodiment of the present invention shown in FIGS. 22-24 utilizes the same electrical connections as those previously described with respect to FIGS. 4 and 12.

Figure 25:
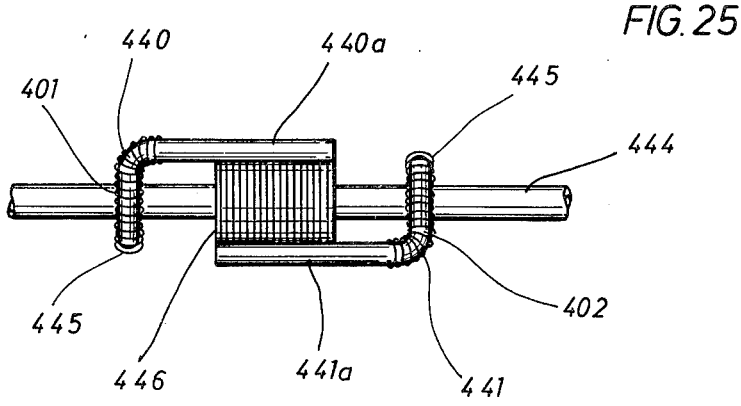
FIG. 25 is a plan view of one embodiment of the flow probe of the present invention.

With reference now to FIG. 25, there is shown a plan view of another embodiment of a flow probe constructed in accordance with the present invention. Generally, this embodiment is similar to that shown in FIGS. 15-18, which has been previously described. The embodiment shown in FIG. 25 comprises two ferromagnetic cores 440 and 441, onto which wire 445 is wound to form two electromagnets 401 and 402, respectively. Ferromagnetic cores 440 and 441 may, for example, be made of iron. Each core 440 and 441 is formed into a generally toric configuration.

Still referring to FIG. 25, the electromagnets 401 and 402 are preferably disposed in the probe in a plane substantially perpendicular to the longitudinal axis of the probe. The ends 440a and 441a of cores 440 and 441 are extended in a plane substantially parallel to the longitudinal axis of the probe, thereby establishing the poles of the electromagnets 401 and 402. Electrodes (not shown) are disposed substantially in the gap between the poles of the electromagnets 401 and 402, in the same manner as shown in FIG. 22, and described previously. A central tubing 444 is provided, as previously described, for communication by such means as the passage of wires, optic fibers, or fluids. The toric members 440 and 441 and the electrodes may be suitably bonded to the central tubing 444 by epoxy or other electrically insulating bonding material (not shown) as previously described. Alternatively, the extended poles 440a and 441a and electrodes (not shown) may be suitably secured to a spacer coil 446 prior to being encapsulated as previously described. The embodiment shown in FIG. 25 utilizes the same electrical connections as those utilized by the embodiments of FIGS. 4 and 22 as previously described in conjunction with FIG. 12.

It has been found from recent experimental testing that a flow probe constructed in accordance with the present invention yields voltage outputs greater than or equal to the flow probes of the prior art. Furthermore, the temperature rise above ambient temperature experienced with the flow probe of the present invention is less than the temperature rise above ambient experienced with flow probes of the prior art. This reduced temperature rise is particularly important in this type of device, since excessive heat dissipated by the probe can be damaging to the fluid or to the vessel into which the probe is inserted. By utilizing the generally toric configuration of the cores as shown in the embodiments of FIGS. 22-25, it has also been found that fewer turns of wire are required to be wound about the cores, since there is less flux leakage between the turns of wire and that the amount of heat generated is reduced accordingly.

Having described the various embodiments of the flow probe of the present invention, the remainder of the specification will be directed toward another important feature which is provided by each of the embodiments of the present invention. This feature is the adaptability for attachment of additional devices to the distal end of the flow probe, thereby permitting multiple measurements in a fluid in a vessel to be made simultaneously. Communication between the distal device and the proximal end of the catheter is accomplished through the probe without sacrificing probe performance. As aforementioned, a flow probe with a ferromagnetic core has not heretofore been constructed which has the capability to have additional devices attached to its distal end without sacrificing probe performance. Without loss of generality, the attachment of additional devices will be described with primary reference to the embodiment of the flow probe of the present invention shown in FIG. 4.

With reference first, however, to FIG. 19, if no additional attachment is desired to be made to the embodiment of the flow probe of the present invention, the end thereof may be encapsulated by suitable bonding material, for example epoxy, to form an arcuate tip 190 as shown. This procedure may be utilized with any of the embodiments of the invention herein described.

With reference now to FIG. 4, central tubing 44 extends beyond the region of the electromagnets if additional devices are to be attached to the distal end of the flow probe. Bushing 46 is attached to the portion of the central tubing 44 extending beyond the distal end of the probe, and bushing 46 is provided as means for attaching additional devices to the probe. FIG. 5 illustrates the encapsulation of the probe with the bushing 46 still exposed.

With reference now to FIG. 9, additional devices, a fluid gathering opening, or catheter extension, may be attached to the distal end of the flow probe. For example, a section of a catheter extension 90 is attached by means of an interference fit between end 90a of the lumen of catheter extension 90 and bushing 46. Suitable cement is additionally utilized to seal the interference fit. Catheter extension 90 may, for example, have attached to its distal end a pressure transducer such as the type disclosed in U.S. Pat. No. 3,748,623 to Millar.

If a pressure transducer such as the type disclosed in the patent to Millar is coupled to the distal end of the flow probe of the present invention, central tubings 91 and 44 would be utilized as a conduit for the wires which electrically connect the pressure transducer to the connector at the proximal end of the catheter. In this case, central tubing member 44 additionally serves as a shield for the wires to the pressure transducer to prevent interference between the signal carried in these wires and the voltage applied to the electromagnets of the flow probe.

The foregoing description of the invention has been directed in primary part to a particular preferred embodiment in accordance with the requirement of the Patent Statutes and for purposes of explanation and illustration. It will be apparent, however, to those skilled in this art that many modifications and changes in the specific apparatus utilized may be made without departing from the scope and spirit of the invention. For example, the various flow probes herein described could be attached to the distal end of the catheter, with additional devices located intermediate the flow probe and the proximal end of the catheter. It is applicant's intention in the following claims to cover such modifications and variations as fall within the true spirit and scope of the invention.

What is claimed is:

1. A fluid-velocity flow probe for insertion into a vessel carrying conductive fluid in a subject, which probe is suitable for attachment to the distal end of a catheter, which probe develops a voltage which is proportional to the velocity of the conductive fluid passing the probe, and which prope comprises:
   a housing;
   means for attaching the housing to a catheter;
   two electromagnets disposed in the housing of the probe for generating two separate magnetic fields, which electromagnets have ferromagnetic cores with gaps between poles;
   two electrodes located in the housing with outer surfaces for fluid-electrode interface, said outer surfaces being exposed to the conductive fluid, each electrode being disposed such that the exposed outer surface for the fluid-electrode interface is substantially in the gap between the poles of the respective electromagnets;
   electrical conductors associated with said electromagnets and electrodes;
   electrically insulating bonding material encapsulating the electromagnets and forming the housing, the bonding material being formed to permit exposure of the outer surfaces of the electrodes so that conductive fluid flowing past the probe will come in direct contact with the electrodes.

2. The flow probe of claim 1 wherein the electromagnets are disposed so as to provide two separate magnetic fields on substantially opposite sides of the housing.

3. The flow probe of claim 1, wherein each of the electromagnets comprises:
   a ferromagnetic core with windings, which core is formed into a generally U-shaped configuration, thereby establishing the poles of the electromagnet at the ends of the core and which core is disposed in the housing in a plane substantially parallel to the longitudinal axis of the housing and in spaced relationship with the other electromagnet so formed.

4. The flow probe of claim 3, wherein it additionally comprises:
   tubing which is disposed in the housing to provide a communicating channel through the length of the probe.

5. The flow probe of claim 1, wherein each of the electromagnets comprises:
   a ferromagnetic core with windings, which core is formed into a generally toric configuration and is disposed in the housing in a plane which forms an angle with the longitudinal axis of the housing with a gap between the ends of the core to establish the poles of the electromagnet.

6. The flow probe of claim 5, wherein the ends of the core are extended in a plane substantially parallel to the longitudinal axis of the housing.

7. The flow probe of claim 5, wherein it additionally comprises:
   tubing which is disposed in the housing provide a communicating channel through the length of the housing.

8. The flow probe of claim 1, wherein each electromagnet comprises:
   a ferromagnetic core with windings of wire, which core is formed into a generally toric shape with a gap between the ends of the core to establish the poles of the electromagnet, which core is disposed in the housing in a plane substantially perpendicular to the longitudinal axis of the housing and in spaced substantially parallel relationship with the other electromagnet.

9. The flow probe of claim 8, wherein the ends of the core which establish the poles of the electromagnet are extended in a plane substantially parallel to the longitudinal axis of the housing.

10. The flow probe of claim 9, wherein it additionally comprises:
    tubing which is disposed in the housing to provide a communicating channel through the length of the housing.

11. The flow probe of claim 8, wherein it additionally comprises:
    tubing which is disposed in the housing to provide a communicating channel through the length of the housing.

12. The flow probe of claim 1 wherein:
    the ferromagnetic core of each electromagnet is formed into a generally U-shaped configuration with windings of wire jointly encompassing both cores, and wherein such cores are disposed in the housing with the open ends of each core spread apart to generate two separate magnetic fields in the housing.

13. The flow probe of claim 12, wherein the arcuate end portions of the U-shaped cores are spread apart and wherein the probe additionally comprises:
    tubing which is disposed between the separated arcuate ends of the cores to provide a communicating channel through the length of the housing.

14. A fluid-velocity flow probe for attachment to a catheter and for insertion into a vessel carrying conductive fluid, comprising:
   an elongated housing having a pair of indentations formed on substantially opposite sides of the exterior of the housing;
   means for attaching the housing to a catheter;
   a pair of electromagnets located in the housing for generating separate magnetic fields in each of the indentations with magnetic flux in a direction generally perpendicular to the longitudinal axis of the housing, the electromagnets providing magnetic flux in each indentation in the same direction when voltage is applied;
   an electrode associated with each electromagnet and disposed in each of the indentations with the outer surface of each electrode exposed to form a fluid-electrode interface between the electrodes and the conductive fluid in the region substantially between the poles of each elect romagnet;
   electrical conductors associated with each of said electromagnets and electrodes; and
   an insulating material encapsulating the electromagnets, which forms the housing, and supporting the electrodes.

15. The flow probe of claim 14, wherein it additionally comprises:
   tubing which is disposed in the housing to provide a communicating channel through the length of the housing.

16. The flow probe of claim 14, wherein the electromagnets comprise two U-shaped ferromagnetic cores disposed in spaced substantially parallel relation on either side of the longitudinal axis of the housing.

17. The flow probe of claim 14 wherein the electromagnets comprise toric ferromagnetic cores mounted in spaced substantially parallel relationship encircling the longitudinal axis of the housing.

18. The flow probe of claim 17 wherein the ends of the cores are extended in planes substantially parallel to the longitudinal axis of the housing with a gap between the ends of the cores to establish the poles of the electromagnets.

19. The flow probe of claim 14 wherein the housing includes a cylindrical tube having slots and the insulating material has indentations at the slots.

20. The flow probe of claim 14 wherein the electromagnets comprise two toric ferromagnetic cores disposed in the housing in a plane which forms an angle with the longitudinal axis of the housing.

21. The flow probe of claim 20, wherein the ends of the cores are extended in planes substantially parallel to the longitudinal axis of the housing with a gap between the ends of the cores to establish the poles of the electromagnets.

22. A fluid-velocity flow probe for insertion into a vessel carrying conductive fluid in a subject, which probe is suitable for attachment to the distal end of a catheter, which catheter comprises a central lumen and electrical conductors between its proximal and distal ends, which probe develops a voltage which is proportional to the velocity of the conductive fluid passing the probe, and which probe comprises:
   a housing;
   means for attaching said housing to a catheter;
   two electromagnets disposed in the housing of the probe for generating two separate magnetic fields, wherein each electromagnet comprises a ferromagnetic core with gaps between poles and windings having a start and a stop winding, said windings being wound on each ferromagnetic core in the same manner between the start and stop windings, and wherein electrical continuity is provided between the stop winding on the first ferromagnetic core and the start winding on the second magnetic core;
   a center-tap conductor electrically connected to the point of electrical continuity between the stop winding on the first ferromagnetic core and the start winding on the second ferromagnetic core;
   two electrodes located in the housing with outer surfaces for fluid-electrode interface, said outer surfaces being exposed to the conductive fluid, each electrode being associated with an electromagnet and being disposed such that the exposed outer surface for the fluid-electrode interface is substantially in the gap between the poles of the electromagnet;
   means for electrically connecting one conductor in the catheter to the start winding on the first ferromagnetic core, for connecting a second conductor in the catheter to the stop winding on the second ferromagnetic core, and for connecting a third conductor in the catheter to be center-tap conductor;
   means for connecting the electrodes to a fourth and a fifth conductor in the catheter; and
   electrically insulating bonding material encapsulating the electromagnets and forming the housing of the probe, the bonding material being formed to permit exposure of the outer surfaces of the electrodes to the conductive fluid so that conductive fluid flowing past the probe will come in direct contact with the electrodes.

23. The flow probe of claim 22, wherein each electromagnet comprises a ferromagnetic core with windings, which core is formed into a generally U-shaped configuration, thereby establishing the poles at the ends of the core, and wherein each electromagnet is disposed in the housing in a plane substantially parallel to the longitudinal axis of the housing and in spaced relationship with the other electromagnet so formed.

24. The flow probe of claim 23, wherein it additionally comprises:
   tubing which is disposed in the housing to provide a communicating channel through the length of the housing.

25. The flow probe of claim 22, wherein each electromagnet comprises a ferromagnetic core with windings, which core is formed into a generally toric shape with a gap between its ends, which core is disposed in the housing in a plane substantially perpendicular to the longitudinal axis of the housing and in spaced relationship with the other electromagnet.

26. The flow probe of claim 25, wherein the ends of the core are extended in a plane substantially parallel to the longitudinal axis of the housing.

27. The flow probe of claim 25, wherein it additionally comprises:
   tubing which is disposed in the housing to provide a communicating channel through the length of the housing.

28. The flow probe of claim 26, wherein it additionally comprises:

tubing which is disposed in the housing to provide a communicating channel through the length of the housing.

29. The flow probe of claim 22, wherein each electromagnet comprises a ferromagnetic core with windings, which core is formed into a generally toric configuration and is disposed in the housing in a plane which forms an angle with the longitudinal axis of the housing, with a gap between the ends of the core to establish the poles of the electromagnet.

30. The flow probe of claim 29, wherein it additionally comprises:

tubing which is disposed in the housing to provide a communicating channel through the length of the housing.

31. The flow probe of claim 29, wherein the ends of the core are extended in a plane substantially parallel to the longitudinal aixs of the housing.

32. The flow probe of claim 31, wherein it additionally comprises:

tubing which is disposed in the housing to provide a communicating channel through the length of the housing.

* * * * *